(12) United States Patent
Lopez Zavala

(10) Patent No.: US 8,772,019 B2
(45) Date of Patent: Jul. 8, 2014

(54) IN-SITU SYSTEM FOR AEROBIC HEAT TREATMENT OF BIODEGRADABLE ORGANIC WASTE

(75) Inventor: Miguel Angel Lopez Zavala, Monterrey (MX)

(73) Assignee: Instituto Tecnologico y de Estudios Superiores de Monterrey, Monterrey (MX)

( * ) Notice: Subject to any disclaimer, the term of this patent is extended or adjusted under 35 U.S.C. 154(b) by 1054 days.

(21) Appl. No.: 12/744,053

(22) PCT Filed: Jun. 27, 2008

(86) PCT No.: PCT/MX2008/000082
§ 371 (c)(1),
(2), (4) Date: May 20, 2010

(87) PCT Pub. No.: WO2009/066971
PCT Pub. Date: May 28, 2009

(65) Prior Publication Data
US 2010/0248353 A1    Sep. 30, 2010

(30) Foreign Application Priority Data
Nov. 20, 2007    (MX) .................... MX/A2007/014509

(51) Int. Cl.
*C12M 1/02*      (2006.01)
*B09B 3/00*      (2006.01)
*C05F 17/02*     (2006.01)
*C05F 17/00*     (2006.01)

(52) U.S. Cl.
CPC ............. *B09B 3/00* (2013.01); *B09B 3/0083* (2013.01); *C05F 17/0063* (2013.01); *C05F 17/02* (2013.01); *C05F 17/027* (2013.01)
USPC ............. 435/290.2; 435/290.1; 435/290.3; 435/290.4; 435/252.3; 435/262.5; 435/286.1

(58) Field of Classification Search
CPC ...... B09B 3/00; B09B 3/0083; C05F 17/0063; C05F 17/02; C05F 17/027; C05F 17/0276
USPC ......... 422/198, 209; 435/290.1, 290.2, 290.3, 435/290.4, 252.3, 262.5, 286.1
See application file for complete search history.

(56) References Cited

U.S. PATENT DOCUMENTS 5,839,375 A    11/1998  Kimberlin
8,043,558 B2   10/2011  Chambe et al.

FOREIGN PATENT DOCUMENTS

GB    2333771 A    8/1999
(Continued)

OTHER PUBLICATIONS

English translation of JP09-47747.*
(Continued)

*Primary Examiner* — Michael Marcheschi
*Assistant Examiner* — Shanta G Doe
(74) *Attorney, Agent, or Firm* — Baker & McKenzie LLP

(57) ABSTRACT

The proposed invention is an in-situ system for aerobic heat treatment of biodegradable organic waste, comprising a bioreactor made up of a dish-shaped decomposition chamber. The decomposition chamber has a lid at the top through which an air extraction device is connected. The air extraction device enables fresh air to enter the decomposition chamber and a preparation for a device supplies the biodegradable organic waste. The decomposition chamber is also connected to a system of pipes which convey a hot fluid from the supply tank into a plurality of minitubes located longitudinally on the inner perimeter of the decomposition chamber, and into a shaft that forms part of the mixing mechanism. A centrifugal pump conveys the same fluid, which is now "cold", from inside the minitubes and shaft to a solar collector, to heat it, before delivering it to a storage tank for subsequent recirculation.

12 Claims, 7 Drawing Sheets

(56) References Cited

FOREIGN PATENT DOCUMENTS

| JP | 9-47747 | A | 2/1997 |
| JP | 9-124385 | A | 5/1997 |
| JP | 3027823 | B2 | 4/2000 |
| JP | 2003-145106 | A | 5/2003 |
| JP | 2006-263418 | A | 10/2006 |
| WO | 02084178 | A1 | 10/2002 |
| WO | 2007076594 | A1 | 7/2007 |
| WO | WO2007076594 | * | 7/2007 |

OTHER PUBLICATIONS

International Search Report, PCT/MX2008/000082, dated Nov. 3, 2008, 4 pages.
International Preliminary Report on Patentability, PCT/MX2008/000082, dated Jun. 1, 2010, 6 pages.

* cited by examiner

IN-SITU SYSTEM FOR AEROBIC HEAT TREATMENT OF BIODEGRADABLE ORGANIC WASTE

CROSS-REFERENCE TO RELATED APPLICATIONS

This application is a 35 U.S.C. Section 371 of PCT/MX2008/000082, filed Jun. 27, 2008, which claims priority to Mexico Application No. MX/a/2007/014509 filed Nov. 20, 2007, which are incorporated herein by reference in their entirety.

OBJECT OF THE INVENTION

This invention describes an in-situ system for the aerobic heat treatment of biodegradable organic waste.

BACKGROUND OF THE INVENTION

The patent application JP 1998-300324A describes a device for treating and decomposition of sanitary organic wastes (feces, urine, and toilet paper), kitchen wastes, and manure from ranching operations. Said patent application, includes a device built of stainless steel which includes a decomposition chamber that is partially filled with a sawdust matrix, a mixing mechanism powered by an electric motor, an electric heating system to raise the temperature in the decomposition chamber, and an air extraction system to create circulation therein, from the inside of the lavatory to the outside. The decomposition chamber is parabolic in form protected by a stainless steel cover that also serves as a base and support for the mixing mechanism and motor that powers it. The mixing mechanism is placed lengthwise in the chamber. It is made of stainless steel and has a shaft which supports it, through radial bars, two coils found towards the center and at one of its ends, the shaft connects to a transmission which is in turn connected to an electric motor. The heating system is made up by a series of Teflon electrical resistors placed lengthwise and crosswise spaced equidistantly on the outside wall of the chamber and the action of the motor and activation of the heating system are controlled by a microprocessor. Said patent application (JP 1998-300324A) presents disadvantages for use in Mexico, as well as in other countries, due to the climatic and economic reality of these countries. Some of these disadvantages are described below:

The cost of manufacturing the bioreactor is high when using stainless steel as its building material. This makes the system inaccessible for the Mexican market; for this reason this patent application proposes innovations to the design of the decomposition chamber that allows a diversification of the building materials without putting the integrity of the chamber at risk when exposed to an elevated pH, salinity, or temperature, present therein.

The mixing system does not guarantee uniform distribution of the biodegradable organic wastes throughout the bioreactor chamber, which affects the capacity for degradation of the system due to the fact that the opening used to introduce the organic wastes is eccentric. As a result of an analysis of the mixture of the material introduced, this invention proposes a central opening to solve this problem.

Heating of the decomposition chamber is accomplished with electrical resistors attached to the decomposition chamber's external wall, but only part of the heat generated by the electric resistors is actually transferred to the sawdust matrix through the wall of the decomposition chamber, and the rest is lost to the exterior, which causes considerable repercussions in the cost to operate the system. In contrast, in the patent application here proposed, heating of the sawdust matrix is performed with a device located on the inside of the decomposition chamber which uses solar energy, and therefore does not require electric power to create heat.

Patent application JP 3027823 (1998) also uses a heating system (electric), as in the previous patent application, which is used to accelerate biological reactions and to adjust the humidity content resulting in high energy consumption. The mixing system is vertically configured with horizontal arms in the bottom of the decomposition chamber, which support vertical curved blades. The arms contain air diffusers through which air is supplied to the sawdust matrix creating an atmosphere conducive to aerobic degradation.

Patent application JP 2006-263418A replaces the electric heating system with conventional and non-conventional electric power sources like solar, wind, and others with a solar heater connected to a supply tank that powers a heat transfer device placed on the exterior of the decomposition chamber wall and, similar to patent application JP 1998-300324A1, this placement of the transfer device is not efficient due to the resistance presented by the heat transfer chamber wall.

The background of the in-situ system for aerobic heat treatment of biodegradable organic waste, which is the object of this invention, is found in the technical reports of step I and II on the development of sustainable systems for water supply and purification in rural and urban zones, presented by Dr. Miguel Angel Lopez Zavala (technician in charge) during 2005; that includes in said research reports: an in-situ system for the differentiated treatment of domestic waste water, that includes a Bio-Health device imported from Japan because it was not possible to acquire this type of Bio-Health device in Mexico. But during research, it was possible to identify opportunities to improve the Bio-Health device acquired in Japan, which later gave rise to a additional line of research, that culminated in this patent application named: "In-situ system for aerobic heat treatment of biodegradable organic waste" that overcomes the deficiencies in the previous patent applications through the innovative design of the decomposition chamber and a device that makes the heat transfer more efficient and allows the reduction of the losses thereof, which makes it a new system for aerobic heat treatment of biodegradable organic waste.

The potential of the system which is the object of this invention lies in that it makes it possible to provide sustainable treatment of organic wastes, such as: sanitary wastes (feces, urine, and toilet paper); manure from cattle operations; meat wastes; traces of blood; organic wastes from restaurants, housing, food industry, and agro-industry; and organic sanitary wastes in rural and urban areas without access to water supply systems and sewage services.

The problems that the invention solves are:
a) With respect to systems for the management and traditional treatment of organic wastes:
  In-situ treatment, consequently eliminating the cost for transportation of the organic wastes,
  High biodegradation rates, thus systems are compact and easy to operate,
  Recovery of nutrients contained in organic wastes in an easy, economical, and effective manner,
  Generation of a compost rich in nutrients, that is easy and safe to handle and may be used as a fertilizer or as a soil conditioner,
  It does not generate bad odors because it uses an aerobic biological process.

Allows the use of renewable energy for the operation of the system.

Does not require specialized personnel for its operation.

b) With respect to conventional sewage systems:

Holistic solution for full management of human excrement,

Does not require water for its operation, thus can be used in areas where there is no water supply or sewage system, Reduces the biological contamination of bodies of water and soil with organic material, nutrients, pathogens, and micro-contaminants (medications and hormones), Reduction in water consumption per inhabitant by approximately 30%, Applicable in scattered rural communities where conventional water and gray water management systems would be a heavy financial burden, Eliminates bad odors in the lavatory, Makes the recovery of nutrients possible in a simple and economical manner.

c) With respect to similar sewage systems:

Low construction, operation, and maintenance costs,

Greater efficiency in mixing the sawdust matrix,

Use of alternative energy (solar, wind, to give just a few examples), for its operation, Greater efficiency in the transfer of heat from the heating system, Lower heat losses through the walls of the reactor tank.

DETAILED DESCRIPTION OF THE INVENTION

Figure 1:
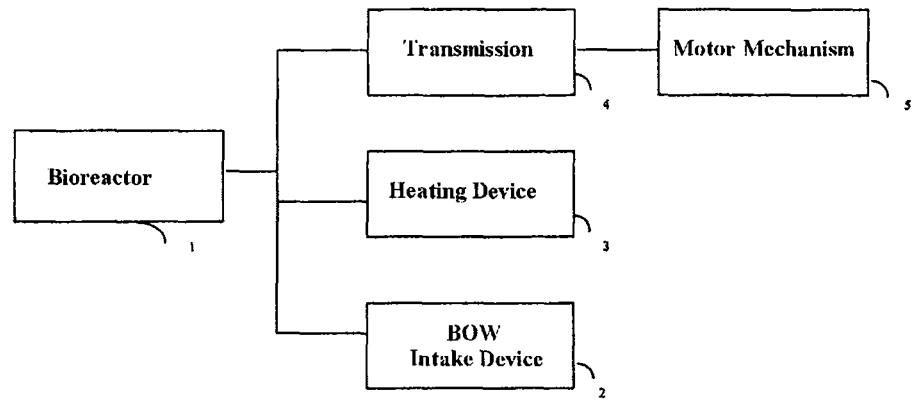
FIG. 1. General diagram of the in-situ system for aerobic heat treatment of biodegradable organic waste.

The in-situ system for aerobic heat treatment of biodegradable organic waste, which is the object of this invention, includes a bioreactor (1) that is connected to an input device for biodegradable organic waste (2), a heating device (3), and a transmission (4) which is powered by a motorized mechanism (5).

Figure 2:
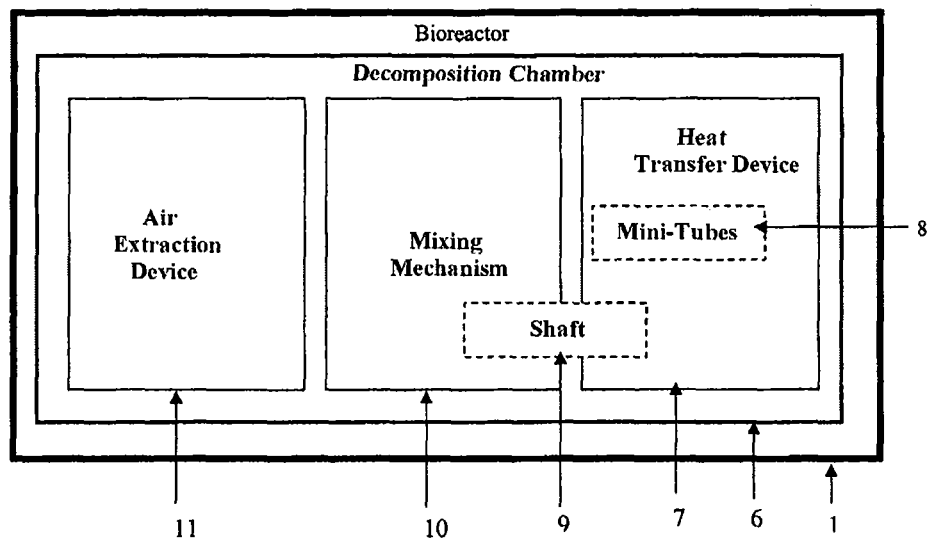
FIG. 2. Schematic illustration of the bioreactor components.
Figure 3:
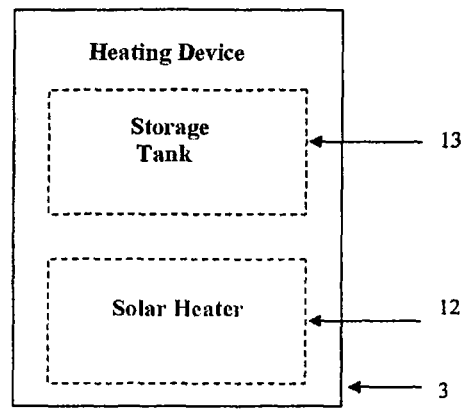
FIG. 3. Schematic illustration of the heating device components.

In FIG. 2, the bioreactor can be seen made up of a decomposition chamber (6) in parabolic shape that holds a sawdust matrix. The decomposition chamber (6), includes: a heat transfer device (7), that comprises a plurality of mini-tubes (8) and a shaft (9), through which a fluid is circulated that is heated via the solar heater (12) of the heating device (3), the heat of the hot liquid that passes through the inside of the shaft (9) and the inside of the plurality of mini-tubes (8) is transfer by conduction-convection to the sawdust matrix contained in the decomposition chamber (6), but the increase in temperature does not provide a condition sufficient to break down the biodegradable organic wastes (BOW), and therefore, it also contains a mixing mechanism (10) to incorporate air and distribute the BOWs into the sawdust matrix. The mixing mechanism (10) is placed lengthwise in the decomposition chamber, and comprises a shaft (9) that supports at least two coils found and connects to a transmission (4) which is powered by a motor mechanism (5). The decomposition chamber (6) also comprises a air extraction device (11), that allows "fresh" air to enter which is rich in oxygen to the decomposition chamber and to extract air saturated with humidity from the inside of the decomposition chamber that makes the process of degradation in aerobic conditions possible.

Figure 4:
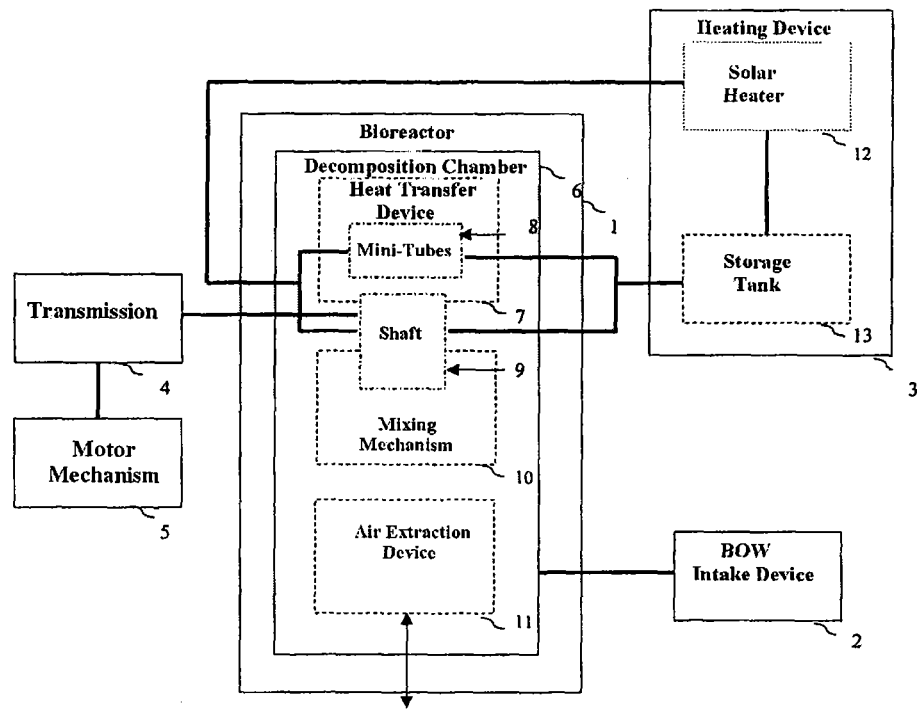
FIG. 4. Schematic illustration with broken lines showing the components of the in-situ system for aerobic heat treatment of biodegradable organic waste.

As was mentioned above, the bioreactor (1) is connected to the heating device (3), and said device comprises: A solar heater (12) used to heat a cold fluid that comes from the heat transfer device (7). Said fluid, once hot, is stored in a storage tank (13) from which, it is directed to the heat transfer device (7) through which it circulates and by conduction-convection transmits heat to the sawdust matrix and to the BOW. FIG. 4 shows the interconnection between the different elements of the system described above.

It is important to mention that the "in-situ system for aerobic heat treatment of biodegradable organic waste" may be installed on the ground or below it, according to the necessities of the project, with which the space available for the project is optimized.

The elements making up the system here proposed are described below in greater detail for the purpose of having a greater understanding of the operation thereof.

Figure 5:
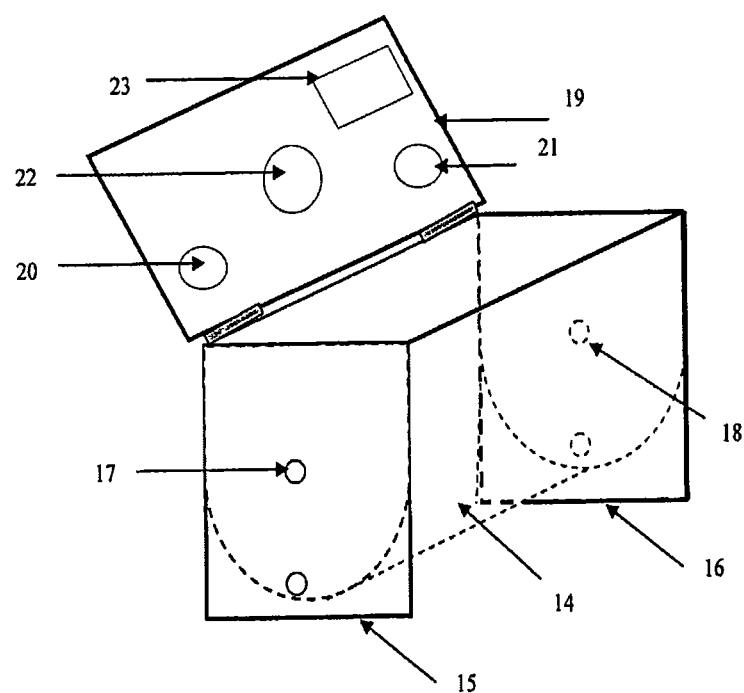
FIG. 5. Isometric view of the open decomposition chamber.

The bioreactor (1) comprising:

A decomposition chamber (6), illustrated in FIG. 5, it is optionally made of galvanized iron laminate, fiberglass, or high temperature resistant polymer. But, no matter what material is used, it is a parabolic shaped plate (14) connected to a pair of parallel plates, one on each side, with the same characteristics that act as side walls (16 and 16). The first side wall (15) presents a first preparation (17) in the center, that is supported by a bushing, one of the ends of the shaft (9) that connects to the transmission (4), and a second preparation (18) located in the center of the second side wall (16) to be supported by bushings, the other end of the shaft; both side walls (15 and 16), protrude from under the bottom of the parabolic plate at least 5 cm from the floor to keep the parabolic plate from contacting (14) the floor. Closing the upper opening of the parabolic plate (14), a first lid (19) is used that is fully attached with screws and/or hinges to the parabolic plate and to the side walls to allow occasional opening and closing of the decomposition chamber (6). The inside of the decomposition chamber (6) is lined with epoxy or a polymer resistant to high temperatures, salt concentrations, and an elevated pH.

The first lid (19), has 4 preparations in the form of holes in its surface (20, 21, 22, and 23).

The first two holes (20 and 21) are located on each end of the lid, and both have the same diameter (10 cm) and to each of them a first extractor tube (24) and a second extractor tube (25) is connected forming part of the air extraction device (11).

The third hole (22) is located at the center of the first lid (19) and has a diameter greater than 10 cm, preferably 20 cm. From this third hole a cylindrical and peripheral wall (26) extends upwards from the first lid (19) and therein assembly with a device is permitted in order to introduce the BOWs into the decomposition chamber.

The fourth hole (23) is rectangular in shape and is placed on one of the ends of the first lid (19), and it is through this opening that the compost generated is extracted. Its dimensions are greater than those of the third hole and has a second lid (27) that has been prepared for a perfect fit around its around its periphery or to be held using hinges to allow the possibility of being opened and closed.

Figure 6:
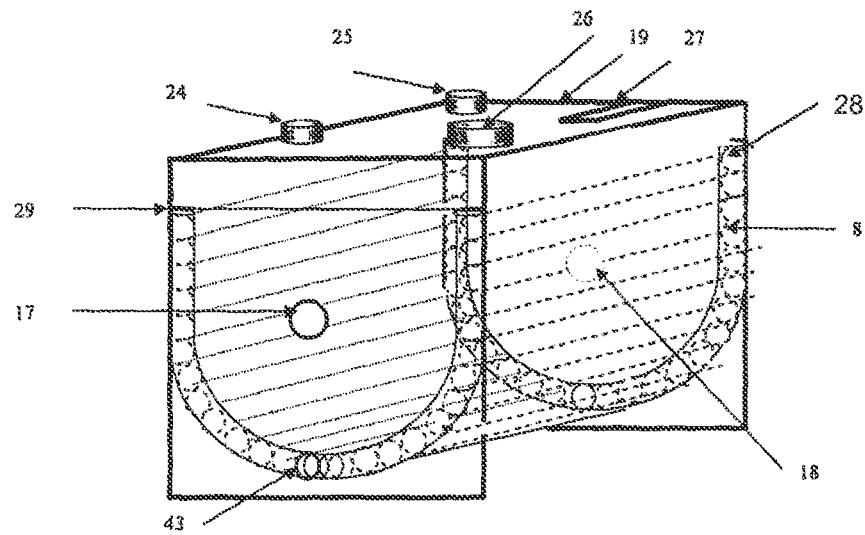
FIG. 6. Isometric view of the closed decomposition chamber.
Figure 7:
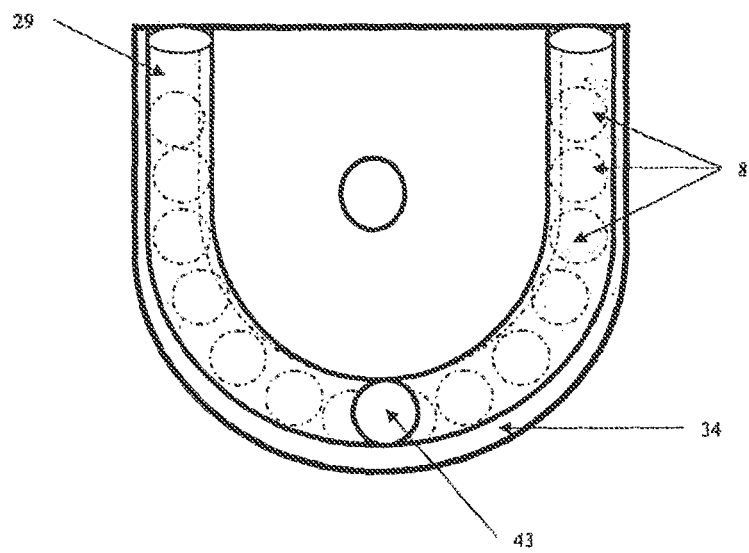
FIG. 7. Side view of the decomposition chamber.

Within the decomposition chamber is found a heat transfer device (7) comprising: the plurality of mini-tubes (8) and the shaft (9); the plurality of mini-tubes (8) are shorter than the decomposition chamber (6), and are placed lengthwise therein, in contact with each other (see FIG. 6) partially embedded in a layer of insulating material (34) attached to the inside surface of the parabolic plate, in such a way that 50% of the exterior surface of the mini-tubes is in direct contact with the sawdust matrix and the other 50% embedded in the layer of insulating material. The purpose of the layer of insulating material (34) is to avoid the transfer and loss of heat to the exterior through the walls of the parabolic plate, in such a way that the totality of the heat transferred through the plurality of mini-tubes (8) may be used to evaporate the water contained in the BOWs that are introduced into the bioreactor (1). Additionally the mini-tubes are soldered at a 90° angle, at one end to a curved hot fluid guide tube (28), and at the other end to a curved cold fluid collector tube (29), both curved tubes follow the curvature of the decomposition chamber (6) and are located on the inside of the decomposition chamber (6), one at each end. The curved tubes (28 and 29) are threaded (43) which connects to a hot fluid guide tube (30) coming from the storage tank (13) as are the lateral ends of the shaft (9), and at the other end to a cold fluid collector tube (31), which is directed to the solar heater (12). The inside of the shaft (9), has a greater diameter than that of the mini-tubes (8), and to guarantee the flow of hot fluid in the mini-tubes and in the shaft, it is necessary that the guide tube (30) has a regulator valve (32); and to ensure that the cold fluid that comes from inside the shaft and from the plurality of the mini-tubes arrives at the solar heater, a centrifugal pump (33) which makes it possible to maintain continuous circulation of the fluid.

An essential element of the bioreactor is the mixing mechanism (10), that consists of a built-in part made of stainless steel, in order to resist high salt concentrations, high temperatures, an elevated pH, and twisting.

The mixing mechanism (10), consists of a hollow shaft (9), placed lengthwise on the inside of the decomposition chamber, and supported by the lateral walls (15 and 16) of the decomposition chamber (6). The mechanical union between the shaft and the walls is via bushings, the hollow shaft protrudes from the side, walls (15 and 16) of the decomposition chamber (6), to allow assembly with the transmission (4) through one of its ends, and coupling to the cold fluid collector tube (31), and through the opposite end (that also protrudes from the decomposition chamber) coupling with the hot fluid guide tube (30). It is preferable to place the transmission at the same end of the shaft that connects to the cold fluid collector tube.

Figure 8:
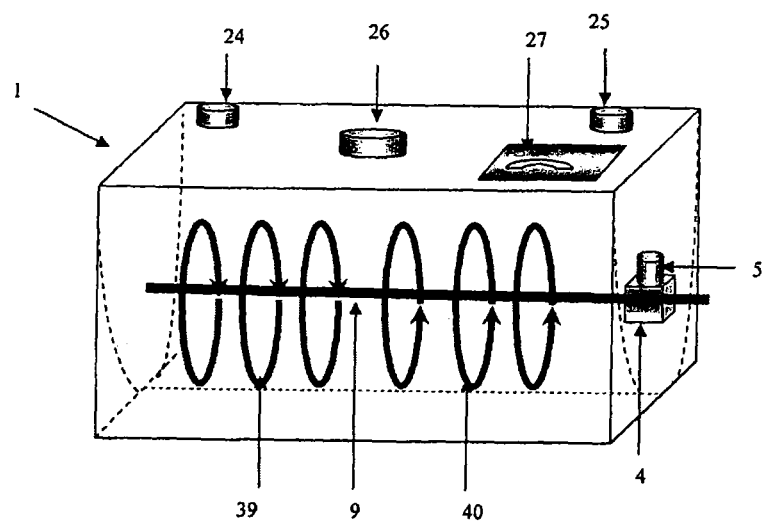
FIG. 8. Front view of the bioreactor of the in-situ system for aerobic heat treatment of biodegradable organic waste.
Figure 9:
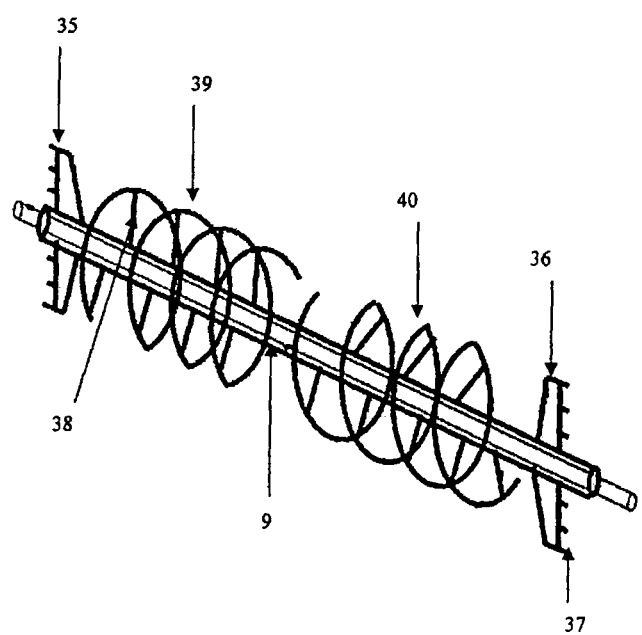
FIG. 9. Isometric view of the mixing mechanism.
Figure 10:
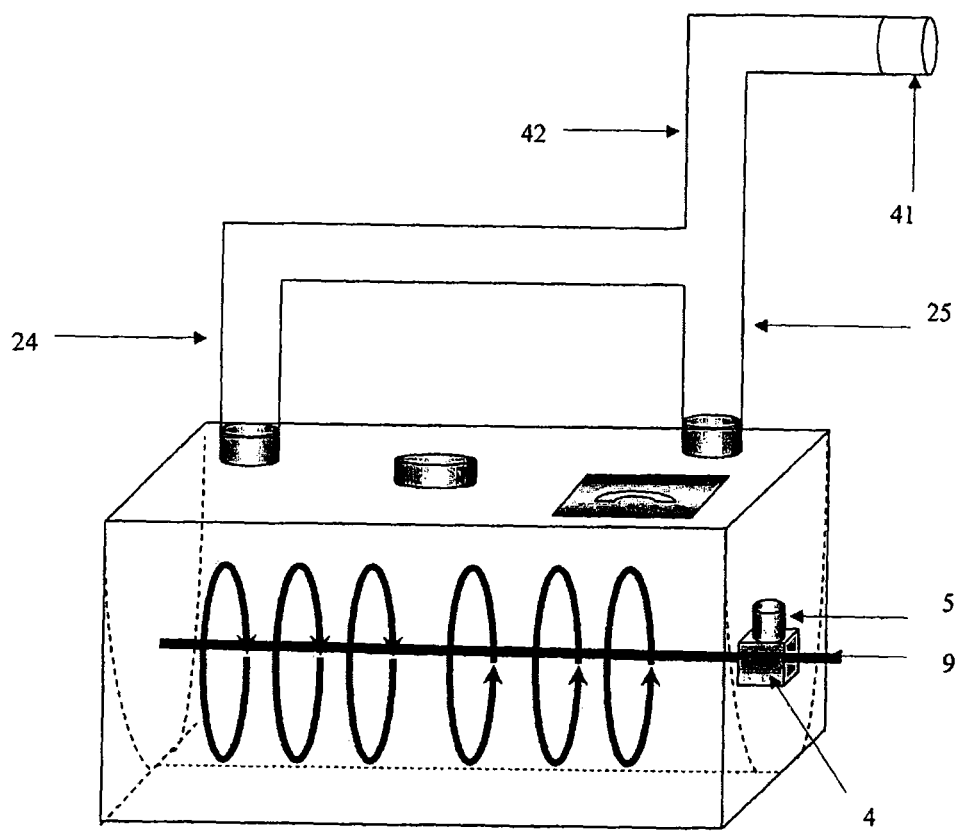
FIG. 10. Schematic illustration of the bioreactor and the air extraction device.
Figure 11:
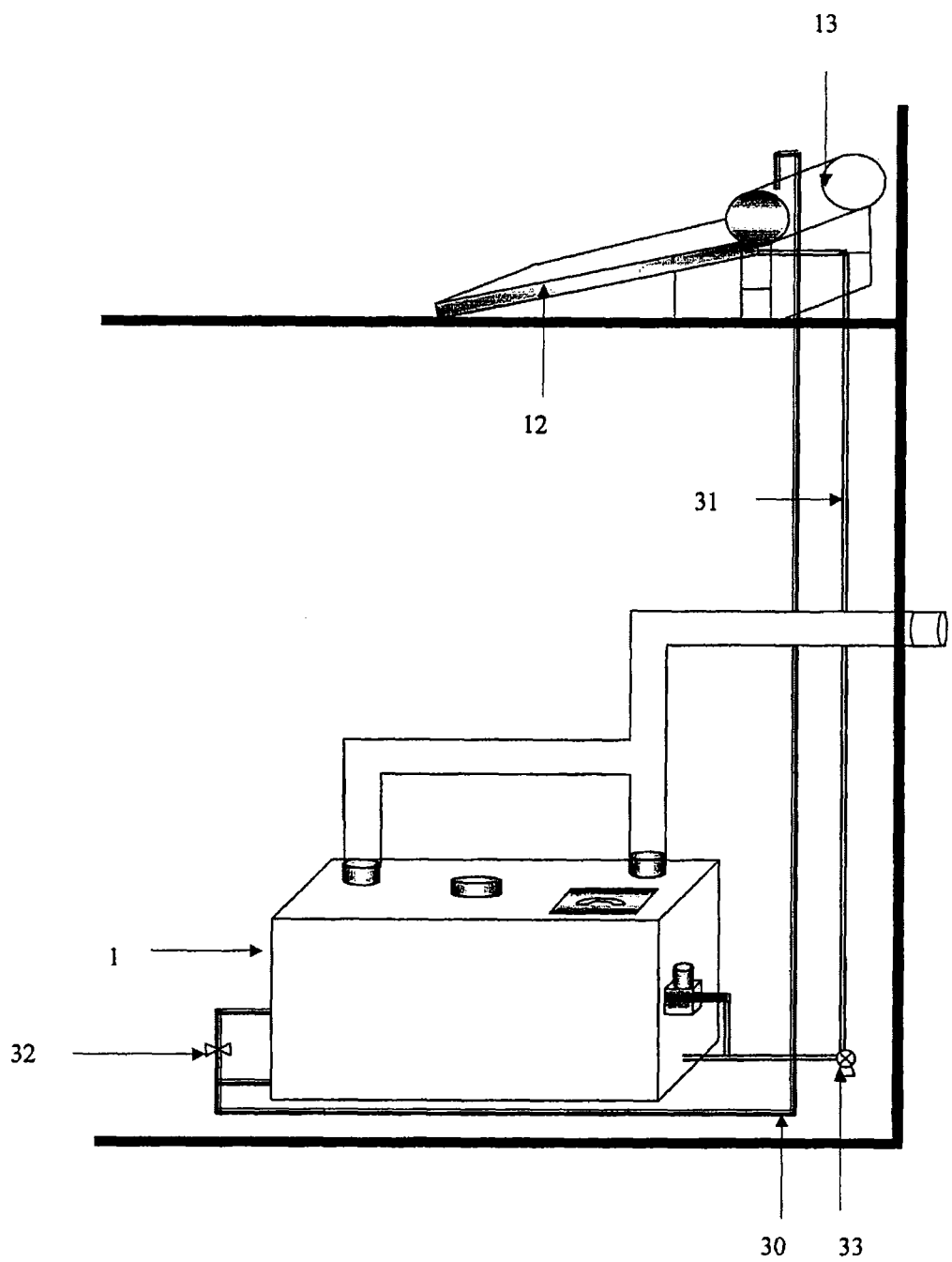
FIG. 11. Schematic illustration of the in-situ system for aerobic heat treatment of biodegradable organic waste.

In FIG. 8, detail of the shaft is shown (9). Each of its ends is comprised of a first and second sweeper (35 y 36), joined together by soldered points. The sweepers (35 y 36) consist of a trapezoidal structure in which the longer surface is parallel to the side walls of the decomposition chamber (6), also, said surface presents a plurality of indentations (37), designed to mix the sawdust matrix and/or the accumulated compost close to the side walls (15 and 16) of the decomposition chamber (6), making the mixing process more efficient. Along the shaft's (9) entire length a plurality of radial bars (38) are soldered, that in turn support a first group of coils (40). These coils are oriented in a direction that is opposite the neighboring coil and the crests of the coils are at an equidistance from each other of 20 cm.

As already mentioned, the shaft (9) is connected to the transmission (4) that transfers the rotary movement produced by a motor mechanism (5), which may be an electrical or mechanical motor; the speed of rotation of the mixing mechanism is 2 rpm; activation of the mixing mechanism (10) is performed in cycles, where each cycle includes 3 complete revolutions or turns, two clockwise, and the third rotation counter clockwise.

As can be seen, the shaft (9) performs a double function. One of these is to permit circulation of the hot fluid that transfers heat to the sawdust matrix by convection-conduction; and because it forms part of the mixing mechanism (10).

The air extraction device (11) includes: A first and second extraction tube (24 and 25) and an extractor (41); where the extraction tubes (24 and 25) are connected to the first holes in the ends (20 and 21) of the first lid (19), to later converge into a single extractor tube (42) that extends to the point of discharge; the extractor (41) is installed in this single extractor tube (42). One should always try to protect it from the weather; the extractor (42) may be powered by wind, electricity, or may be mechanical and operate continuously.

Having sufficiently described my invention, I feel that it is an innovation and therefore, claim the content of the following clauses as my exclusive property:

The invention claimed is:

1. An in-situ system for aerobic processing of biodegradable organic waste comprising:
   a. a bioreactor connected to an input device, a heating device and a transmission powered by a motor mechanism, wherein said bioreactor comprises a decomposition chamber formed by a parabolic shaped plate and a pair of parallel plates joined to side ends of the parabolic shaped plate, thereby closing off the decomposition chamber around its sides;
   b. a first lid connected to an upper part of said decomposition chamber;
   c. an air extraction device, wherein the air extraction device is connected to a first hole and a second hole in the first lid and the input device is connected to a third hole located in a center of the first lid;
   d. the extraction device located within the decomposition chamber;
   e. a mixing mechanism consisting of a hollow shaft, wherein said hollow shaft is placed lengthwise in the decomposition chamber and is supported by a lateral wall of the decomposition chamber, the hollow shaft being connected at one end to the transmission;
   f. a heat transfer mechanism located inside the decomposition chamber, wherein said heat transfer mechanism comprises the hollow shaft of the mixing mechanism; and
   g. a plurality of mini-tubes having lengths which are smaller than the decomposition chamber, wherein said mini-tubes are placed lengthwise and in direct contact with each other thereby adopting to a form of the decomposition chamber, further wherein said mini-tubes are embedded in a layer of insulating material attached to an inside surface of the parabolic shaped plate, such that 50% of an exterior surface of the mini-tubes is exposed to direct contact with contents of the decomposition chamber and the other 50% is embedded in the layer of the insulating material, the mini-tubes are soldered at about a 90 degree angle at one end to a curved hot fluid guide tube and at the other end to a curved cold fluid collector tube, the curved hot fluid guide tube and the curved cold fluid collector tube are embedded in the decomposition chamber and are threaded to connect to a hot fluid guide tube and a cold fluid collector tube respectively.

2. The in-situ system for aerobic processing of biodegradable organic waste of claim 1, wherein the side ends of the parabolic shaped plate protrude from the bottom of the parabolic shaped plate by at least 5 cm.

3. The in-situ system for aerobic processing of biodegradable organic waste of claim 1, wherein the first and second holes in the first lid have a same diameter.

4. The in-situ system for aerobic processing of biodegradable organic waste of claim 1, wherein the first and second holes in the first lid have diameters of about 10 cm.

5. The in-situ system for aerobic processing of biodegradable organic waste of claim 1, wherein the third hole has a diameter of about 20 cm.

6. The in-situ system for aerobic processing of biodegradable organic waste of claim 1, wherein the third hole has a diameter greater than 10 cm and less than 20 cm.

7. The in-situ system for aerobic processing of biodegradable organic waste of claim 1, wherein the decomposition chamber is made of fiberglass.

8. The in-situ system for aerobic processing of biodegradable organic waste of claim 1, wherein the decomposition chamber is made of a polymer, which is resistant to high temperatures.

9. The in-situ system for aerobic processing of biodegradable organic waste of claim 1, wherein the decomposition chamber is made of galvanized iron.

10. The in-situ system for aerobic processing of biodegradable organic waste of claim 1, wherein the decomposition chamber is lined with epoxy or a polymer resistant to high temperatures, salt concentrations, and an elevated pH.

11. The in-situ system for aerobic processing of biodegradable organic waste of claim 1, wherein the first lid is connected to the decomposition chamber with screws.

12. The in-situ system for aerobic processing of biodegradable organic waste of claim 1, wherein the first lid is connected to the decomposition chamber with hinges.

* * * * *